United States Patent [19]

Cabannes

[11] Patent Number: 4,702,114
[45] Date of Patent: Oct. 27, 1987

[54] DEVICE FOR WITHDRAWING AND CONDITIONING SAMPLES OF MATERIALS IN SOLID, LIQUID OR GASEOUS FORM, FOR THE PURPOSE OF ANALYSIS THEREOF

[75] Inventor: Claude Cabannes, Eygalieres, France

[73] Assignee: OMYA S.A., France

[21] Appl. No.: 727,089

[22] Filed: Apr. 25, 1985

[30] Foreign Application Priority Data

May 7, 1984 [FR] France .................................. 84 07244

[51] Int. Cl.⁴ ......................... G01N 1/20; G01N 1/22
[52] U.S. Cl. ........................... 73/863.85; 73/863.11; 73/863.54
[58] Field of Search .......... 73/863.85, 863.54, 863.01, 73/863.11, 863.12, 863, 863.83, 863.84, 863.86, 863.81, 863.82

[56] References Cited

U.S. PATENT DOCUMENTS

| | | | |
|---|---|---|---|
| 1,521,545 | 12/1924 | Kistler. | |
| 3,115,782 | 12/1963 | Echtler, Jr. | 73/863.85 |
| 3,747,411 | 7/1973 | McDermott et al. | 73/863.54 |
| 3,949,614 | 4/1976 | Abonnenc | 73/863.83 |
| 4,024,765 | 5/1977 | Abonnenc | 73/863.83 |
| 4,262,533 | 4/1981 | Jaeger | 73/863.11 |
| 4,433,587 | 2/1984 | Risdal | 73/863.54 |

FOREIGN PATENT DOCUMENTS 2015126 11/1970 Fed. Rep. of Germany.
691725 10/1979 U.S.S.R. .................... 73/863.11

Primary Examiner—Tom Noland
Attorney, Agent, or Firm—Jones, Day, Reavis & Pogue

[57] ABSTRACT

A device for withdrawal of a fixed volume of powdered, liquid or gaseous material from a withdrawal zone and for conditioning the withdrawn materials for the purpose of analysis which comprises a retractable cylindrical probe in which there is provided a cavity of known capacity, a retractable sleeve coaxially disposed over the probe for permitting or preventing access to the cavity, a substantially closed chamber in which the probe and sleeve are disposed for reciprocal movement into and out of the withdrawal zone, whereby the probe and sleeve may be extended from the chamber into the withdrawal zone, the sleeve may be retracted to fill the cavity, the sleeve may be extended to seal the cavity, the probe and sleeve may be retracted from the withdrawal zone back into the closed chamber, and finally, the sleeve may again be retracted to permit conditioning of the withdrawn material.

9 Claims, 9 Drawing Figures

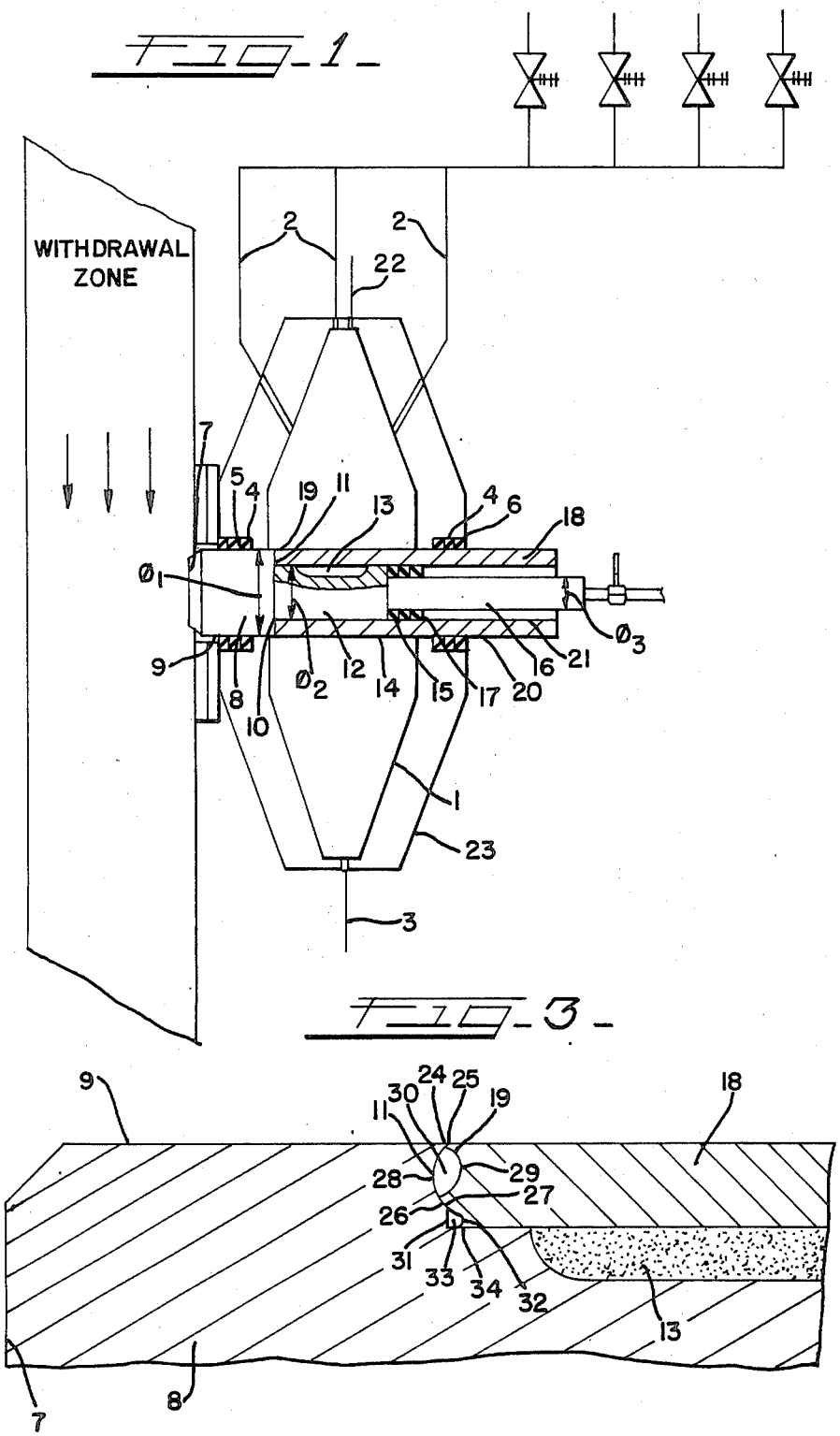

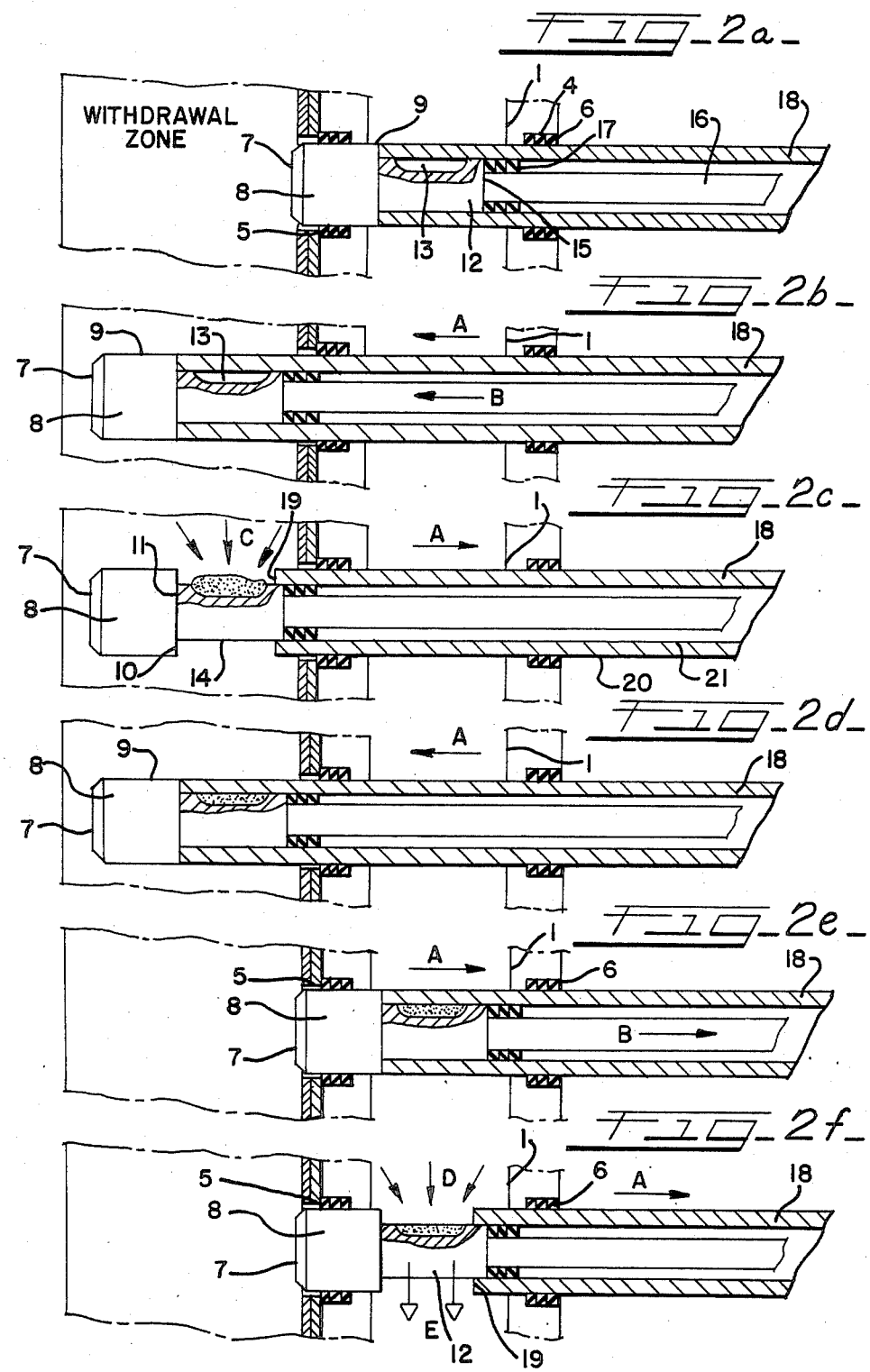

DEVICE FOR WITHDRAWING AND CONDITIONING SAMPLES OF MATERIALS IN SOLID, LIQUID OR GASEOUS FORM, FOR THE PURPOSE OF ANALYSIS THEREOF

BACKGROUND OF THE INVENTION

The invention relates to a device for automatic withdrawal of a gauged volume of pulverulent solid, liquid or gaseous materials present in a withdrawal zone in which the prevailing pressure is greater than, equal to or less than atmospheric pressure, and for conditioning of these withdrawn materials for the purpose of analysis thereof.

For a long time, industries, such as, for example, the chemical industry, the metallurgical industry, the agri-foodstuffs industry, etc., have used raw materials which they convert to intermediate products or to finished products which man exploits, uses or consumes for his survival, comfort, etc.

The processes of transformation of raw materials to intermediate products or finished products which are pulverulent, liquid or gaseous in form pass through successive stages of working-up, and these require that controls should be carried out, such as controls of, for example, particle size, chemical composition, physical properties, reactivity, purity, and the like.

To perform suitable controls, the expert has to carry out the withdrawal of homogeneous, representative and repeated samples of the products obtained during the conversion of the raw materials, so that they can be examined continuously or discontinuously and that the deficiencies and/or imperfections can be detected and corrected by a rapid intervention, for example, in the conversion process.

For a long time, the technology of withdrawing samples of materials for analysis during industrial processes has consisted of manual equipment for taking samples at places and times which are insufficiently precise for the samples to be beyond dispute for the expert, that is to say, to be representative of a given state at an identified place and a precise moment. It is the case, for example, that in hydrometallurgy, to determine and follow the rate of settling, in a large sized settler (diameter: twenty meters; height: five meters), of a solid phase in an aqueous suspension resulting from the attack of an ore, sampling was carried out by lowering a closed cylindrical measure to a depth which is fixed but only approximate, since it is observed by the unwinding of a length of cable, and then opening and closing the measure again, by manual operation, when it has reached the presumptive withdrawal zone, before raising it again. However, the sampling point of the suspension is never exactly the same from one withdrawal operation to the next, so that the analysis of each withdrawal gives approximate information which is, however, insufficiently objective and representative of the state of settling of the suspension.

Since then, improved devices for withdrawing samples have been proposed. Such devices are capable of carrying out these withdrawals in a precise and methodical manner, without human intervention, in order that each sample withdrawn should be fully representative of the material to be controlled.

An example of an improved device for automatic sample withdrawal is described in Frensh Pat. No. 2,258,108. This device incorporates a cylindrical horizontal probe in which there is provided a longitudinal recess of specified capacity and of shape suitable for the nature of the material to be sampled. Driving means drive the probe in longitudinal repriprocating motion, and guiding means direct the recess in the probe upwards in the filling position, when the probe is inside the withdrawal zone, and downwards in a discharge position in a receptor zone when it has been removed from the withdrawal zone. The probe is equipped with a shutter consisting of a cylindrical coaxial sleeve, provided with an opening of dimensions at least equal to those of the recess formed in the probe. This shutter is driven in longitudinal reciprocating motion by driving means and in rotatory motion by other guiding means designed to rotate the sleeve relative to the probe. The recess in the probe coincides with the opening in the sleeve at the times when the probe is in position for withdrawal and for discharge of the sample, and the recess is masked during the intermediate phases of the probe.

This device, however, has certain disadvantages. For example, it does not prevent leakage between the zones for withdrawal and for discharge of the sample. Nor does it protect the physical characteristics of the sample between withdrawal and discharge from infiltration of particles foreign to the sample. For this reason, a first improvement of this device was proposed and described in Patent FR A No. 2,271,559. This improved device incorporates a fixed, no longer movable, coaxial cylindrical shutter (sleeve) sealed integrally to the separation partition between the withdrawal and discharge zones, the abovementioned opening in the shutter being located in the discharge zone facing downwards. The withdrawal probe moves inside the fixed cylindrical shutter, its translational and rotational movements being guided by a continuous groove located on the shutter and a radial pin integral with the probe projecting into the groove.

The device described in Patent FR A No. 2,258,108 also has another disadvantage, however which appears during operation of the probe. When the probe is removed from the withdrawal zone, it wedges a particle of sample material between the rear edge of its recess and the end of the shutter which opens into the withdrawal zone. To limit this disadvantage, a second improvement of the abovementioned device was claimed in Patent FR A No. 2,288,307. This second improvement consists in providing the front end of the probe, situated forward of the recess, with a flat or gap of depth greater than the particle size of the material to be sampled.

As a result of this, at the end of the retraction movement of the probe, this flat (or gap) forms with the inner wall of the shutter a space which enables the particles of material to be released without them being wedged or disrupted.

This device and its improvements, which offer undeniable advantages with respect to the prior art in the field of sampling of granular materials, nevertheless possess other disadvantages than those already mentioned, which can be of major importance and especially troublesome for their industrial use. A first disadvantage is, for example, the definite lack of imperviousness to leakage between the withdrawal and discharge zones and between the withdrawal probe, and coaxial cylindrical shutter (whether fixed or otherwise) and the guiding means. Another disadvantage resides in the fact that the shape of the probe in the recess portion is selfdestructive for the gaskets which would be installed in this device in place of the self-luricating materials. Finally, a further disadvantage, which results from those mentioned above, relates to the impossibility with this device of carrying out withdrawals of materials in the liquid phase, such as a solution or suspension, and in gaseous phase, or of carrying out withdrawals of materials whether in the solid, liquid or gaseous state when the withdrawal zone is at a pressure greater or less than atmospheric pressure.

As a result, and by virtue of the above-mentioned disadvantages, the Applicant, continuing his investigations, has discovered and perfected a device for automatic withdrawal, and also for conditioning, of a measured volume of pulverulent solid, liquid or gaseous materials, for the purposes of analysis thereof, in a withdrawal zone in which there prevails a pressure greater than, equal to or less than atmospheric pressure.

SUMMARY OF THE INVENTION

The device according to the invention, which comprises a cylindrical probe in which there is provided a longitudinal recess of exact capacity for withdrawal of the sample, a sleeve coaxial with the probe, means for driving the probe and the coaxial sleeve in a longitudinal reciprocating motion, and also means for sealing and guiding the probe and the coaxial sleeve, is characterized in that it incorporates:

(a) a closed chamber for receiving and conditioning the sample withdrawn, equipped with means for introducing liquid and/or gaseous fluids enabling the materials withdrawn to be conditioned and then the chamber to be washed, and means for outgassing and removal of the conditioned materials, cylindrical sections or cylinders which serves as guides for the cylindrical probe and as supports for the front and rear seals located at opposite sides adjacent the chamber, (b) a cylindrical withdrawal probe which moves longitudinally in the cylinders mentioned in paragraph (a), incorporating three distinct portions:

the front portion, of diameter $\phi_1$ and length at least equal to the thickness of the front seals mentioned in paragraph (a), the rear face of which is equipped with a shoulder which provides for the functions of applying pressure, of centering and of preventing leakage, the middle portion, of diameter $\phi_2$ less than $\phi_1$, equipped with the cavity of specified capacity intended for withdrawal of the material in the withdrawal zone, the rear face of which is also equipped with a shoulder, the rear portion, of diameter $\phi_3$ less than $\phi_2$, connected by a known means to the longitudinal driving means, and bearing a gasket at its front end, (c) The coaxial sleeve moving in the cylinders mentioned in paragraph (a), of external diameter exactly equal to $\phi_1$ of the front portion of the cylindrical probe of paragraph (b), provides, on the one hand for continuity of size with the front portion of the cylindrical probe, and on the other hand for the closing of the cavity intended for the withdrawal of the materials by longitudinal movement, the front face of the sleeve coming to bear on the shoulder of the front portion of the cylindrical probe of paragraph (b), and the external and internal surfaces of the sleeve preventing by way of seals, leakage between the closed chamber of paragraph (a), the withdrawal zone and the atmosphere.

According to the invention, the device pursues the aim of carrying out instantaneously and automatically the withdrawal of a measured volume of materials to be analyzed automatically and remotely. The materials analyzed may be, for example, materials withdrawn at one or more points of any industrial process involving the mechanical and/or chemical conversion of raw materials such as minerals, the separation of liquid and solid phases, the mixing of materials, the transfer of materials during conversion, the packaging of finished materials, etc.

The withdrawn materials which constitute the samples can be in pulverulent solid form, liquid form such as a solution, an emulsion or a suspension of a solid phase in a liquid phase, or finally in gaseous form consisting of only one gas or a mixture of gases.

The withdrawal zone, containing the materials to be withdrawn for analysis, can be, for example, a zone for storage of raw materials or materials in the course of conversion or finished materials. The withdrawal zone may also be a reaction or conversion zone, such as, for example, a chemical reactor, grinder, settler, phase separator, roasting kiln or fluidized decomposition bed. Alternatively, the withdrawal zone may be a transfer zone, such as, for example, a pipeline, fluidized bed, pneumatic conveyor, conveyor belt, etc.

Since the withdrawal is instantaneous and automatic, this withdrawal zone, which is not disturbed by the sample being taken, can be under a pressure greater than, equal to or less than atmospheric pressure. This pressure can only be limited by the shape and quality of the gaskets used.

The materials present in the withdrawal zone can be at widely different temperatures. Thus, for example, the device according to the invention has been tested in a temperature range as broad as $-30°$ C. to $+350°$ C. The device, however, can also operate in a much broader temperature range, depending on the shape and quality of the seals and also on the presence of cooling and/or heating means. Suitable cooling or heating means may be, for example, a double wall or coils of piping enabling heat-transfer or coolant fluids to be circulated around the device.

The closed chamber for receiving and conditioning the sample withdrawn from the withdrawal zone can be subjected to the same pressures and temperatures as the withdrawal zone, but can also be subjected to different pressures and temperatures from those prevailing in the withdrawal zone. The closed chamber for receiving and conditioning the sample is equipped with means for introducing liquid and/or gaseous fluids which enable the materials to be solubilized, to be brought to a state of suspension, emulsion or mixture, or to be converted chemically by a reaction "in situ", then for removing the conditioned sample to a suitable automatic analyzer, and finally for rinsing the chamber after removal of the sample.

The cylinder which passes through the chamber for receiving and conditioning the sample is equipped with front and rear gaskets.

BRIEF DESCRIPTION OF THE DRAWINGS

The invention will be better understood by means of the illustrative description of FIGS. 1 to 4.

FIG. 1 shows a longitudinal section in elevation of a particular embodiment of the device for withdrawal and conditioning of a sample to be analyzed.

FIGS. 2(a) to 2(f) show longitudinal sections in elevation of the cylindrical withdrawal probe and the coaxial sleeve in the six successive phases of a withdrawal, reception and conditioning cycle of a sample.

FIG. 3 shows a longitudinal section of a variant, on the one hand of the shoulder of the rear face of the front portion of the withdrawal probe, and on the other hand of the front face of the coaxial sleeve which bears on the abovementioned shoulder.

DETAILED DESCRIPTION

Figure 4:
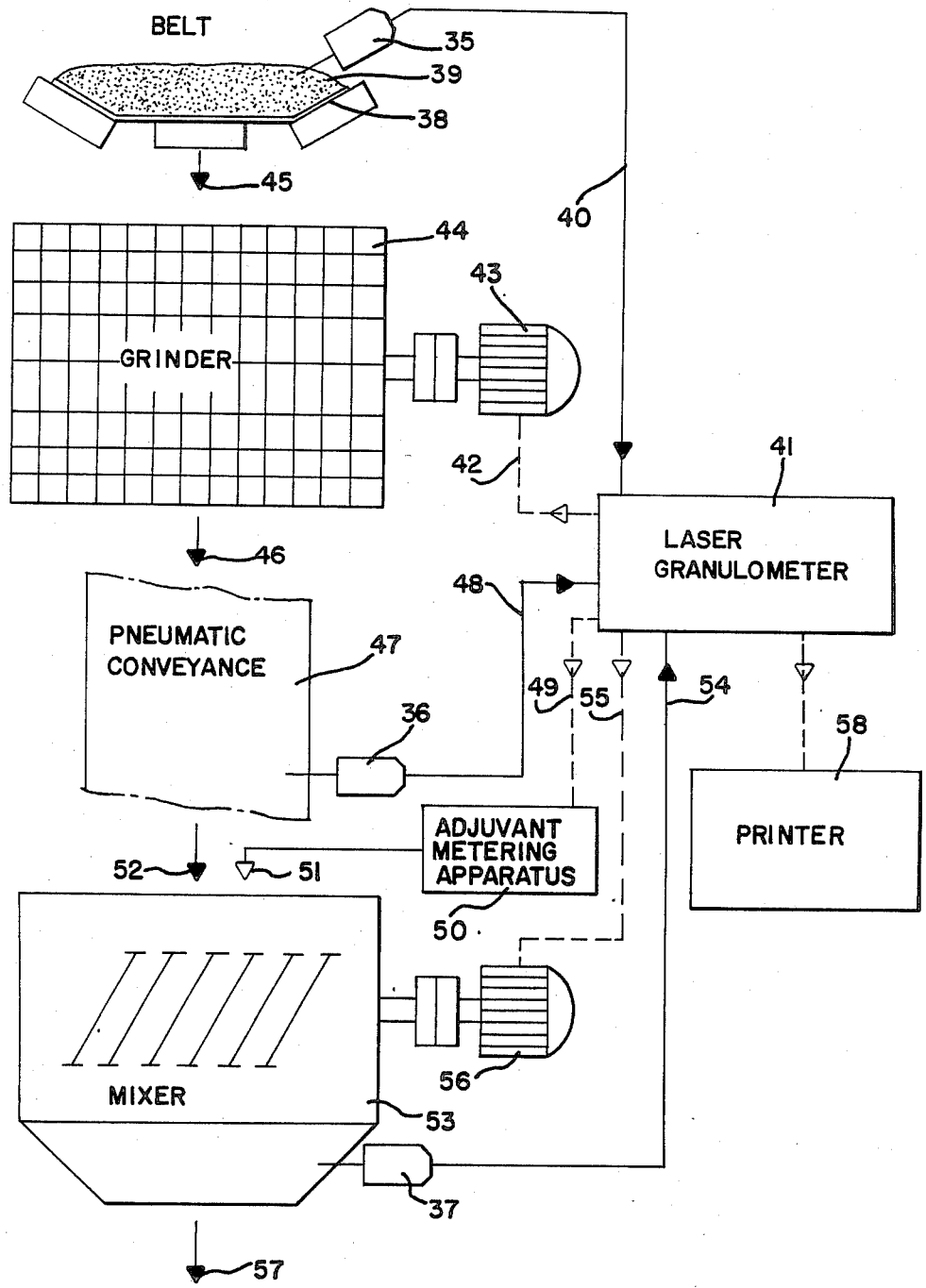
FIG. 4 illustrates an example of an industrial application of the device according to the invention.

Referring to FIG. 1, the device according to the invention first incorporates a closed chamber (1) in which the sample withdrawn in the withdrawal zone is received and conditioned. The chamber (a) is equipped with means (2) for introducing liquid and/or gaseous fluids which enable the sample to be conditioned, that is to say enable the withdrawn materials to be solubilized, brought into suspension or emulsion or caused to react. The means (2) are also used for introducing fluids for washing the chamber. The chamber (1) is also equipped with means for outgassing (22) and means for removing (3) the conditioned materials.

Cylindrical sections (4) which serve as guides and supports for the front (5) and rear (6) seals are positioned at opposite sides adjacent chamber (1).

The device according to the invention next incorporates a withdrawal probe (7) which moves longitudinally in the cylinders (4) of the chamber (1) while being driven in an automatic reciprocating motion by known means (not shown) for control and transmission of motion. The probe (7) is composed of three distinct portions:

the front portion (8), of diameter $\phi_1$ and length at least equal to the thickness of the front seal (5), the outer surface (9) of which is precision-ground and the rear face (10) of which is equipped with a shoulder (11) which provides for the functions of applying pressure, of centering and of preventing leakage.

The middle portion (12), of diameter $\phi_2$ less than $\phi_1$, equipped with the cavity (13) of specified capacity, intended for withdrawal of the material in the withdrawal zone, the external surface (14) of the middle portion being precision-ground and the rear face of the middle portion being equipped with a shoulder (15).

The rear portion (16), finally, of diameter $\phi_3$ less than $\phi_2$, connected by a known means (not shown) to the longitudinal driving means, bearing a gasket at its front end (17).

The device according to the invention finally incorporates a coaxial sleeve (18) which moves longitudinally in the cylinders (4). The external diameter of the sleeve (18) is exactly equal to the diameter $\phi_1$ of the front portion (8) of the withdrawal probe (7). The sleeve (18) provides for continuity of size with the front portion (8) and for the closing of the cavity (13) by longitudinal movement. The sleeve (18) includes a front face (19) which comes to bear on the shoulder (11) of the front portion (8) of the cylindrical probe (7). External (20) and internal (21) surfaces of the sleeve are precision-ground, the sleeve (18) providing by its internal face (21) the imperviousness to leakage between the chamber (1) and the atmosphere by means of the seal (17) when the cylindrical probe (7) moves inside the sleeve. The external face (20) prevents leakage between the withdrawal zone and the chamber (1) by means of the gasket (5), and between the chamber (9) and the atmosphere by means of the gasket (6) when the sleeve (18) moves in the cylinders (4). The closed chamber for receiving and conditioning the sample is also equipped with cooling and/or heating means (23).

FIGS. 2(a) to 2(f) illustrate the operation of the device according to the invention.

FIG. 2(a) shows both the withdrawal probe (7) and the coaxial sleeve (18) at rest.

FIG. 2(b) shows the position in the withdrawal zone of the withdrawal probe (7) and the coaxial sleeve (18) closing the withdrawal cavity (13) when probe and sleeve have been simultaneously introduced in the withdrawal zone, by means which are not shown, according to the arrows (A) for the sleeve (18) and (B) for the probe (7).

FIG. 2(c) shows the probe (7) at rest, but in position for withdrawal of the materials (C) to be analyzed when the coaxial sleeve (18) exposes the cavity (13) by the longitudinal movement represented by the arrow (A).

FIG. 2(d) illustrates the gauging of the withdrawn sample by means of the coaxial sleeve (18) when the sleeve is advanced in the direction of the arrow (A) while the probe (7) is still at rest.

FIG. 2(e) shows the introduction of the sample into the closed reception and conditioning chamber (1) by the simultaneous movement according to the arrows (A and B) of the withdrawal probe (7) and the coaxial sleeve (18).

FIG. 2(f) demonstrates the conditioning of the withdrawn sample by introducing suitable fluids according to (D) and the removal of the conditioned sample according to (E). The longitudinal motions (not shown) of the withdrawal probe (7) and the coaxial sleeve (18) can be provided by mechanical, hydraulic, electrical or pneumatic means. They can be programmed in advance and remote controlled, and are thus carried out without human intervention.

Furthermore, the external surface (9) of the front portion (8) of the probe (7), the external surface (14) of the middle portion (12) of the said probe, the external (20) and internal (21) surfaces of the coaxial sleeve (18), and the front (5) and rear (6) seals of the probe (7), the shoulders (11) and (15), the gaskets (17) of the rear portion (16) of the withdrawal probe (7), and likewise the continuity of size between the coaxial sleeve (18) of diameter $\phi_1$ and the front portion (8) of the cylindrical probe (7) of the same diameter $\phi_1$ provide for excellent imperviousness to leakage between the withdrawal zone and the chamber, on the one hand, and between the chamber and the atmosphere on the other hand, whatever the relative position of the withdrawal probe (7) and the coaxial sleeve (18) during the cycle of withdrawal of the sample.

The operation of the device as it appears in FIGS. 2(a) to 2(f) is as follows.

Considering the device in the rest position FIG. 2(a), the cavity (13) present in the closed chamber (1) for receiving and conditioning the sample, is closed as a result of the relative position of the withdrawal probe (7) and the coaxial sleeve (18). The imperviousness to leakage between the withdrawal zone, the closed chamber (1) and the atmosphere is very effectively provided by the points (5), (6) and (17) in contact with the precision-ground surfaces (9), (14), (20) and (21). The assembly consisting of the probe (7) and the coaxial sleeve (18) is subjected to a longitudinal movement by suitable means (not shown) and enters the zone for withdrawal of the sample, placing the closed cavity (13) in the zone (FIG. 2b). The coaxial sleeve (18) is then subjected to a reverse longitudinal movement by a suitable means (not shown) while the withdrawal probe remains at rest. The cavity (13) of the probe (7) is then opened and filled, by gravity with the sample to be analyzed (FIG. 2c), while complete imperviousness to leakage is maintained between the withdrawal zone, the chamber (1) and the atmosphere. When the cavity (13) is full, the coaxial sleeve (18) is subjected to a further longitudinal movement which brings its front face (19) to bear in intimate contact with the shoulder (11) of the front portion (8) of the probe. This action provides for the gauging of the withdrawn sample by removing the excess material, and also centers the coaxial sleeve (18) relative to the probe (7), prevents leakage of the cavity (13) (FIG. 2d). When the sample thus gauged is in the cavity (13), the assembly consisting of the probe (7) and the coaxial sleeve (18), in the position where pressure is applied, is subjected to a longitudinal movement (caused by means not shown) and enters the closed chamber (1) for receiving and conditioning the sample, the imperviousness to leakage still being exceptionally well provided between the withdrawal zone, the closed chamber (1) and the atmosphere (FIG. 2e). The coaxial sleeve (18) is then subjected to a further longitudinal movement while the probe (7) remains at rest in the reception and conditioning chamber (1). As a result of this, the cavity (13) is opened and the sample is conditioned by injecting the appropriate fluids according to the arrows (D) (FIG. 2f) before being conveyed outside the chamber (1) to any suitable analysis equipment (not shown).

FIG. 3 shows a longitudinal section in elevation of a variant of the shoulder (11) of the front part (8) of the withdrawal probe (7), and a variant of the front face (19) of the coaxial sleeve (18) which bears on the shoulder (11). In the case of FIGS. 1 and 2a to 2f, the shoulder (11) of the withdrawal probe (7) and the front face (19) of the coaxial sleeve (18) are plane surfaces perpendicular to the axis of the probe. However, some problems can arise when the cavity (13) filled with the sample to be analyzed is closed by the movement of the coaxial sleeve (18) (FIGS. 2c and 2d). In effect, in the particular case where the material withdrawn is a pulverulent solid, one or more particles can remain between the shoulder (11) of the withdrawal probe and the front face (19) of the coaxial sleeve. For this reason shoulder (11) and front face (19) can consist of curved surfaces, the intersecton of which with the plane of longitudinal elevation is shown by a succession of straight or curved lines. In the case of FIG. 3, the shoulder (11) of the withdrawal probe (7) and the front face (19) of the coaxial sleeve (18) are in contact through the knife-edges (24) and (25) which remove particles and through the surfaces (26) and (27). The surfaces (28) and (29) create a first decompression zone (30) which collects the fragments of particles caused by the application of the knife-edge (24) and (25) while the surfaces (31) and (32) create a second decompression zone (33) which receives, through the action of the knife (34) the excess material during the gauging of the sample. In practice, the two decompression zones (30) and (33) collect insignificant amounts of material.

Referring to FIG. 4, an example of industrial application of the device according to the invention is shown. Three withdrawal devices (35), (36) and (37) are installed in an industrial production line for inorganic pigments.

A conveyor belt (38) transports the pre-ground raw material (39). The withdrawal device (35) withdraws a 1 cm$^3$ sample every four minutes, which, after conditioning, is conducted by the pipeline to the Laser granulometer (41). The result of the automatic analysis of the sample, processed by the granulometer computer, causes a command to be issued through (42) to increase, maintain or decrease the activity of the motor (43) operating the grinder (44) at the time when the material (39) enters the grinder (44) by the means (45). At the outlet of the grinder (44), the finely ground material (46) is introduced into a pneumatic conveyance (47) to be taken to another stage of the process. The device (36) according to the invention withdraws and conditions the sample issuing from the pneumatic conveyance (47). The sample withdrawn, representing a volume of 0.25 cm$^3$, is then taken through (48) to the Laser granulometer (41). The analytical result, processed by the granulometer computer, causes a signal to be emitted through (49) to adjust the flowrate of the metering apparatus (50). The metering apparatus supplies through (51) an adjuvant which has to be mixed with the ground material (52), adjuvant and ground material being introduced simultaneously into the mixer (53). Since the mixing operation has to be very homogeneous, the device (37) according to the invention also withdraws every four minutes a 0.5 cm$^3$ sample which, after being conditioned, is conducted through (54) to the Laser granulometer (41). The result of the analysis processed by the computer associated with the granulometer (41) causes the emission of a signal by (55) which acts on the motor (56) to maintain the quality of the mixture at its highest level. Thus, the finished product extracted from the manufacturing sequence through (57) has been followed, by automatic control, step by step, throughout the entire production sequence, thus enabling each stage to be maintained within the quality limits.

All the granulometric analyses have been recorded on a printer (58) coupled to the Laser granulometer (41).

I claim:

1. A device for withdrawal of a fixed volume of powdered, liquid or gaseous material from a withdrawal zone and for conditioning the withdrawn materials for purposes of analysis comprising:
    (a) a retractable cylindrical probe in which there is provided a cavity of known capacity,
    (b) a retractable sleeve coaxially disposed over the probe for permitting or preventing access to the cavity,
    (c) a substantially closed chamber in which the probe and sleeve are disposed for reciprocal movement into and out of the withdrawal zone, said chamber including means for conditioning the material withdrawn by the probe, whereby (1) the probe and sleeve may be extended from the chamber into the withdrawal zone, (2) the sleeve may be retracted to fill the cavity, (3) the sleeve may be extended to seal the cavity, (4) the probe and sleeve may be retracted from the withdrawal zone back into the closed chamber and finally (5) the sleeve may be retracted within the chamber to permit conditioning of the withdrawn material.

2. A device according to claim 1 wherein the chamber includes front and rear seals to prevent leakage into and out of the chamber.

3. A device according to claim 1 wherein the chamber is equipped with heating means.

4. A device according to claim 1 wherein the chambr includes outgassing means.

5. A device according to claim 1 wherein the probe is divided into a front portion, a middle portion and a rear portion and the middle portion contains the cavity of known capacity.

6. A device according to claim 5 wherein the rear portion bears a gasket at a front end thereof to prevent leakage.

7. A device according to claim 5 wherein the sleeve has a front face which abuts against the front portion of the probe at a rear face thereof when the cavity is closed to prevent leakage of the cavity.

8. A device according to claim 7 wherein the front face of the sleeve and the rear face of the front portion are plane surfaces perpendicular to the axis of the probe.

9. A device according to claim 7 wherein the front face of the sleeve and the rear face of the front portion are curved surfaces which form knife-edges at their contact points to prevent entrapment of solid particles between said faces.

* * * * *